United States Patent [19]

Watanabe et al.

[11] Patent Number: 5,291,899
[45] Date of Patent: Mar. 8, 1994

[54] METHOD AND DEVICE FOR MEASURING INTRACRANIAL PRESSURE

[75] Inventors: Yasuo Watanabe, Komae; Hideaki Shimazu, Tokyo, both of Japan

[73] Assignee: Kabushiki Kaisha Nihon M.D.M., Japan

[21] Appl. No.: 693,443

[22] Filed: Apr. 29, 1991

[30] Foreign Application Priority Data

May 10, 1990 [JP] Japan .................................. 2-120450

[51] Int. Cl.⁵ .............................................. A61B 5/00
[52] U.S. Cl. ........................................ 128/746; 604/9; 73/714; 73/715
[58] Field of Search ............... 128/748, 774; 604/9, 604/8, 10; 73/700, 708, 714, 715, 4 R, 753, 756, 726, 727, 729, 730, 731

[56] References Cited

U.S. PATENT DOCUMENTS

| | | | |
|---|---|---|---|
| 4,281,667 | 8/1981 | Cosman | 128/748 |
| 4,441,357 | 4/1984 | Kahn et al. | 128/748 |
| 4,494,411 | 1/1985 | Koschke et al. | 73/724 |
| 4,672,974 | 6/1987 | Lee | 128/673 |
| 4,885,002 | 12/1989 | Watanabe et al. | 604/9 |
| 4,901,735 | 2/1990 | von Berg | 128/748 |
| 4,993,425 | 2/1991 | Kronberg | 128/748 |
| 5,063,936 | 11/1991 | Sato et al. | 128/674 |

FOREIGN PATENT DOCUMENTS

| | | | |
|---|---|---|---|
| 2720455 | 11/1978 | Fed. Rep. of Germany | 128/748 |
| 2384482 | 11/1978 | France | 128/748 |

*Primary Examiner*—Stephen C. Pellegrino
*Assistant Examiner*—Guy V. Tucker
*Attorney, Agent, or Firm*—Bruce L. Adams; Van C. Wilks

[57] ABSTRACT

This invention provides a method for measuring intracranial pressure and a device for the same which enable intracranial pressure to be accurately measured without any conventional calibration using data obtained by previous measurement because they are characterized in that intracranial pressure is measured after a communication valve capable of communicating with the atmosphere is closed following zero point correction of a pressure transducer performed by adjusting the internal pressure of a flexible membrane provided at the tip of a pressing part and filled with a fluid to atmospheric pressure by the operation of the above communication valve.

20 Claims, 8 Drawing Sheets

5,291,899

METHOD AND DEVICE FOR MEASURING INTRACRANIAL PRESSURE

BACKGROUND OF THE INVENTION

1. Field of the Invention

This invention relates to a method for measuring intracranial pressure of a hydrocephalic patient or the like and a device for the same, and more particularly to an improved pressure detector and a method for measuring intracranial pressure by using an improved pressure detector.

2. Prior Art

In neurosurgical diseases associated with a rise in intracranial pressure, generally intracranial pressure should accurately be measured for the clarification of their pathological profiles.

Various means for measuring intracranial pressure have conventionally been proposed, which include one disclosed in Japanese Patent Application No. 135,069/1989.

As shown in FIGS. 6 to 8, it is constituted of an implant A to be implanted in the patient's body and a pressure detector B which is disposed outside the patient's body and which can touch a reservoir for intracranial pressure measurement of the implant A through the scalp 16'.

The implant A comprises a fine tubular brain ventricle catheter 12 to be inserted at its tip portion 12b into a brain ventricle 19 of a patient so as to drain cerebrospinal fluid from the brain ventricle 19, reservoir 11 connected to the catheter 12 and an implant main body 22' consisting of a soft wall made of a silicone resin or the like and fixed on the skull 17 under the scalp 16'. The upper part of the reservoir 11 is provided with a membranous flexible spherical dome 11a for intracranial pressure measurement.

The pressure detector B is provided with a probe 21 protrudably attached to a frame 23, the probe 21 is so constructed that it is pressed toward the spherical dome 11a at a constant speed by means of a screw lever 24 revolving at a constant speed, and the tip portion of the probe 21 is provided with a pressing part 26 having a flexible membrane 25 such as a urethane film which is filled with a liquid 22 (e.g., silicone oil).

The pressure detector B is also provided with a pressure transducer 27 for measuring the pressing pressure of the pressing part 26 and the output signal of the pressure transducer 27 is fed to an amplifier 35' through a lead wire 28. Amplified signals from the amplifier 35' are fed to a recorder 37 such as a printer for recording an amplified signal after receiving it through a lead wire 36 and to a display device 38 such as a CRT for displaying an amplified signal. Symbol 29 represents a return spring.

A method for measuring intracranial pressure by using a device for measuring intracranial pressure having the above structure will be described next. Intracranial pressure can be measured according to the following procedure with the implant A implanted at a predetermined position.

(1) Cerebrospinal fluid is fed through the brain ventricle catheter 12 to the reservoir 11 for intracranial pressure measurement which is implanted on the skull 17 under the scalp 16'. The spherical dome 11a of the above reservoir 11 is outwardly expanded by the pressure of cerebrospinal fluid; the pressure of cerebrospinal fluid within the spherical dome 11a at this point is denoted by Pi.

(2) The pressure detector B is turned on and the measuring operation is started (a time $t_A$ in FIG. 8). At this point, the pressing part 26 is positioned apart from the scalp 16' and in a non-contact state therewith.

Thus, the dome 11a is not pressed by the external force.

(3) Measurement of the pressure $P_O$ of the liquid in the pressing part 26 is started by extending the probe 21 of the pressure detector B at a constant speed until the pressing part 26 touches the above upper dome 11a through the scalp 16' (FIG. 7(a) and a time $t_B$ in FIG. 8).

(4) Pressing of the pressing part 26 against the spherical dome 11a is continued by continuing expansion of the probe 21 at a constant speed. In this state, liquid pressure $P_O$ in the pressing part 26 gradually increases due to the reaction force of cerebrospinal fluid within the spherical dome 11a (the state shown in FIG. 7(b)). Although Pi is higher than $P_O$ at this point, $P_O$ gradually approximates to Pi.

(5) When the pressing part 26 is further pressed against the spherical dome 11a until $P_O$ becomes approximate to Pi, the spherical dome 11a becomes flat (the state shown in FIG. 7(c)). When $P_O$ becomes higher than Pi in due course, the spherical dome 11a begins to curve inwardly (FIG. 7(d) and a time $t_c$ in FIG. 8). The liquid pressure in the pressing part 26 at this point is denoted by $P_1$.

Liquid pressure in the pressing part 26 rapidly decreases temporarily because its capacity increases according to inward curving of the spherical dome 11a (a time $t_d$ in FIG. 8). The liquid pressure in the pressing part 26 at this point is represented by $S_1$.

(6) After the pressing part 26 is further pressed against the spherical dome 11a, the probe 21 is withdrawn at a constant speed; the turning point corresponds to a time $t_e$ in FIG. 8 and the liquid pressure at that point is represented by $P_2$.

(7) Although the inwardly curved spherical dome 11a begins to be restored at the point when Pi becomes approximate to $P_O$ during the process of withdrawing the probe 21 (the liquid pressure immediately before the restoration is denoted by $S_{2x}$) and as the spherical dome 11a is gradually restored, the pressing part 26 is compressed and liquid pressure in it temporarily increases (a time $t_g$ in FIG. 8, the liquid pressure at this point is denoted by $P_3$.), liquid pressure $P_O$ in the pressing part 26 gradually decreases as withdrawal of the probe 21 is continued and returns to the initial pressure level when the part 26 moves apart from the dome 11a (a time $t_h$ in FIG. 8).

Intracranial pressure $S_2$ can be obtained by comparing pressure levels $P_1$, $S_1$, $P_2$ and $P_3$ detected at the times $t_c$, $t_d$, $t_e$ and $t_g$ by the above operation with data obtained by previous measurement using the probe.

SUMMARY OF THE INVENTION

When using the above described conventional pressure detector, calibration using data obtained by previous measurement should be performed in measuring intracranial pressure in order to eliminate measurement errors accompanying changes in the volume of the liquid filled in the pressing part 26 due to heat, and accurate measurement of intracranial pressure is impossible without the calibration.

This invention was devised in order to solve these problems and its object is to provide a method for measuring intracranial pressure and a device for the same which enable intracranial pressure to be accurately measured without any conventional calibration using data obtained by previous measurement, characterized in that intracranial pressure is measured after a communication valve capable of communicating with the atmosphere is closed following zero point correction of a pressure transducer performed by adjusting the internal pressure of a flexible membrane provided at the tip of a pressing part and filled with a fluid to atmospheric pressure by the operation of the above communication valve.

In order to achieve the above object, a method for measuring intracranial pressure according to this invention is characterized in that intracranial pressure is measured, using a device for measuring intracranial pressure which comprises a reservoir for intracranial pressure measurement which is implanted under the skin of a human body and into which cerebrospinal fluid can be introduced from a brain ventricle, a flexible spherical dome for intracranial pressure measurement which is configured to be upwardly projected from the reservoir by the pressure of the cerebrospinal fluid and can bend according to an external force, a pressing part which can be pressed against the spherical dome through the skin, a pressing-part-driving means which presses the pressing part toward the spherical dome at a constant speed, a pressure transducer which can measure the force of the pressing part pressing the spherical dome and a flexible membrane provided at the tip of the pressing part and filled with a fluid, by pressing the flexible membrane of the pressing part against the spherical dome of the reservoir through the skin by means of the pressing-part-driving means after zero point correction of the pressure transducer is performed by communicating the interior of the flexible membrane with the atmosphere. Zero point correction of the transducer is performed by opening a valve which can communicate the interior of the flexible membrane with the atmosphere and then closing the same valve.

A device for measuring intracranial pressure according to this invention is characterized in that it consists of a reservoir for intracranial pressure measurement which is to be implanted under the skin and into which cerebrospinal fluid can be introduced, a flexible spherical dome for intracranial pressure measurement which is configured to be upwardly projected from the reservoir by the pressure of the cerebrospinal fluid and can bend according to the external force and a pressure detector having a pressing part which can be pressed against the spherical dome through the skin, and in that the pressure detector comprises a pressing-part-driving means which presses the pressing part against the spherical dome at a constant speed, a pressure transducer which can measure the force of the pressing part pressing the spherical dome, a flexible membrane provided at the tip of the pressing part and filled with a fluid, an exhaust path which can communicate the interior of the flexible membrane with the atmosphere and a valve provided in the exhaust path.

The above pressure detector has a cylindrical frame and also has the pressing part which is vertically movably fitted inside the frame. The pressing-part-driving means is constituted of a nut attached to the rear end of the pressing part and a motor having a revolving shaft provided with a male thread fitting the nut. The pressure detector also has as the exhaust path an exhaust pipe communicating with the interior of the flexible membrane and the valve is provided in the exhaust pipe. The pressure detector is equipped with a solenoid valve as the valve and a controller which can control the movement of the solenoid valve. In addition, a leg to be mounted on the skin of a human body is attached to the tip portion of the cylindrical frame. The leg is so fitted that its position relative to the cylindrical frame can be properly adjusted by means of a thumbscrew.

BRIEF DESCRIPTION OF THE DRAWINGS

Both of FIGS. 1 and 2 are schematic longitudinal sectional views of a measuring device according to the present invention.

FIG. 6 is a schematic longitudinal sectional view of the measuring device, all of FIGS. 7(a) to (d) are schematic longitudinal sectional views showing the measurement procedure and FIG. 8 is a graph showing results of measurement.

DETAILED DESCRIPTION OF THE PREFERRED EMBODIMENT

A method for measuring intracranial pressure and a device for the same as an example of this invention will be described hereinbelow with reference to the drawings.

Figure 1:
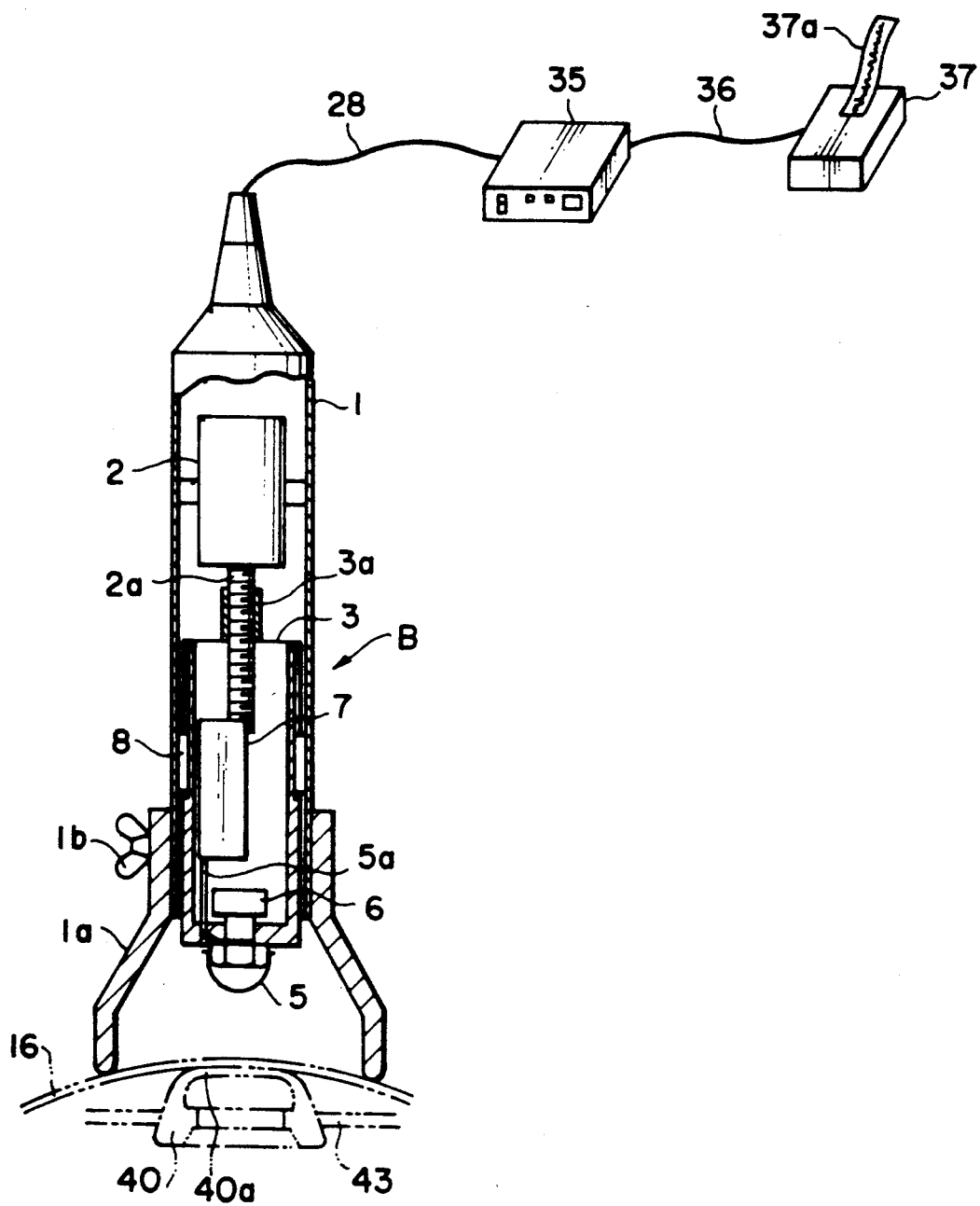
Figure 2:
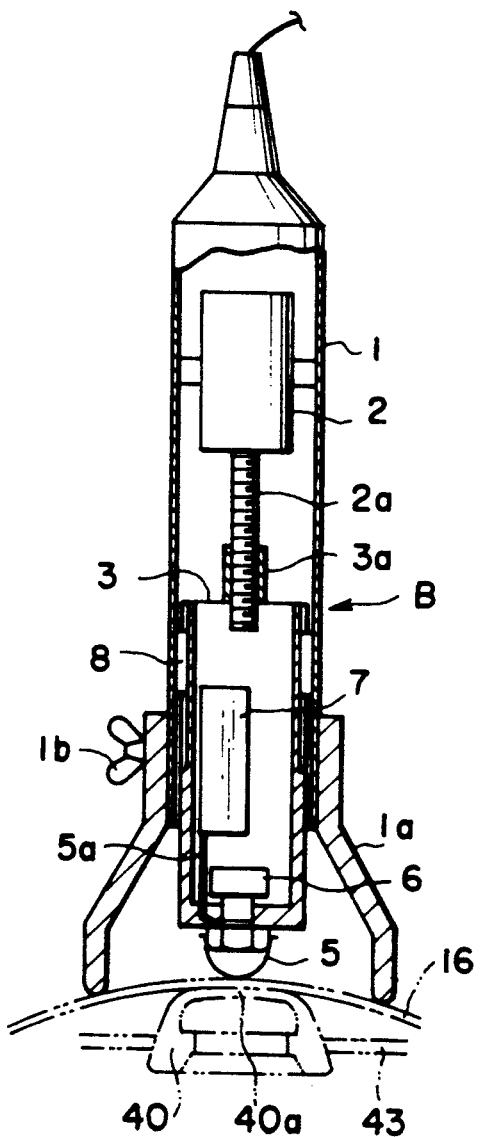

As shown in FIG. 1, the principle of the measurement method and measuring device of this example consists in measuring intracranial pressure by introducing cerebrospinal fluid from a brain ventricle into a reservoir for intracranial pressure measurement which is implanted under the skin of a human body. The device is constituted of a reservoir 40 implanted under the skin 16 and a pressure detector B.

Figure 4:
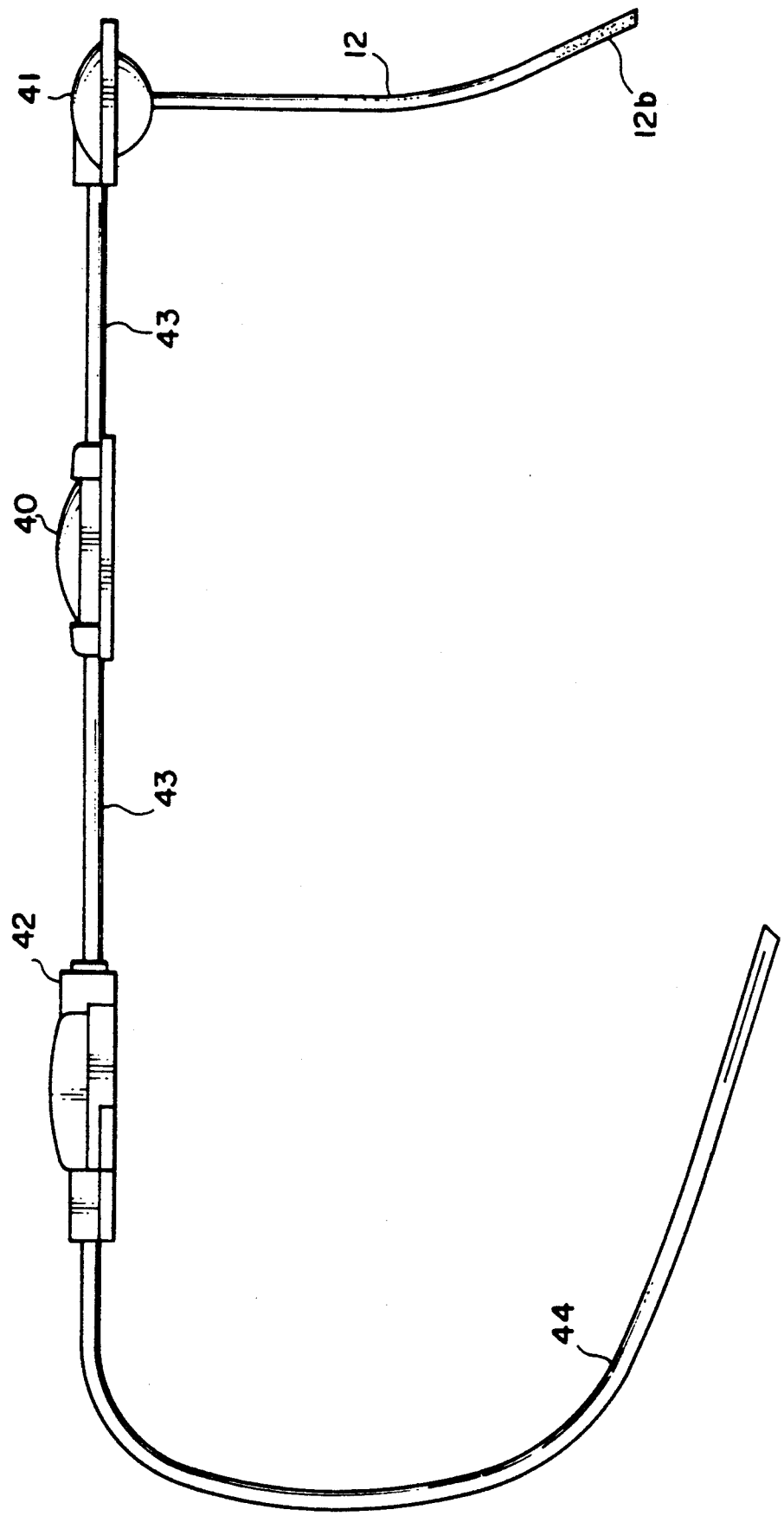
FIG. 4 is a schematic illustration of a brain ventricle shunt system and FIG. 5 is a graph showing an example of measurement record.

The reservoir 40 corresponds to the aforementioned reservoir 11 and in this example is connected to a brain ventricle port 41 through a connection tube 43 and implanted under the skin of the chest or the like as shown in FIG. 4. Cerebrospinal fluid is introduced from a brain ventricle of a patient into the brain ventricle port 41 through a brain ventricle catheter 12. Symbol 40a represents the spherical dome of the reservoir 40. The reservoir 40 is connected through a valve 42 to a catheter 44.

The pressure detector B has a cylindrical frame 1 and a movable pressing part 3 which is so supported that it can only move vertically in the frame 1 through a guide member 8 fixed to the frame 1. The pressing part 3 can be protruded from the lower end opening of the frame 1 at a constant speed by means of a DC motor 2 fitted inside the frame 1.

Symbol 2a represents the revolving shaft of the DC motor 2. The outer surface of the revolving shaft is provided with a male thread and a nut 3a fitting the male thread is fixed to the pressing part 3. Symbol 1a represents a leg attached to the lower end portion of the frame 1 in such a manner that the positional relation between the leg 1a and the frame 1 can be properly adjusted by means of a thumbscrew 1b.

The lower end portion of the pressing part 3 is fitted with a flexible membrane 5 filled with air and a pressure transducer 6 for measuring the internal air pressure of the flexible membrane 5 which constitute a pressure sensor.

The detection signal from the pressure transducer 6 is fed to a controller 35 through a cable 28 and then to a recorder 37 through a cable 36. Symbol 37a represents a recording paper.

The pressure detector B is also equipped with an exhaust pipe 5a communicating with the interior of the flexible membrane 5, and a solenoid valve 7 is connected to the exhaust pipe 5a.

It is desirable that the flexible membrane 5 be made of a membranous highly elastic material and, for example, silicone rubber, fluorine rubber or urethane is suitable for the membrane 5.

Figure 3:
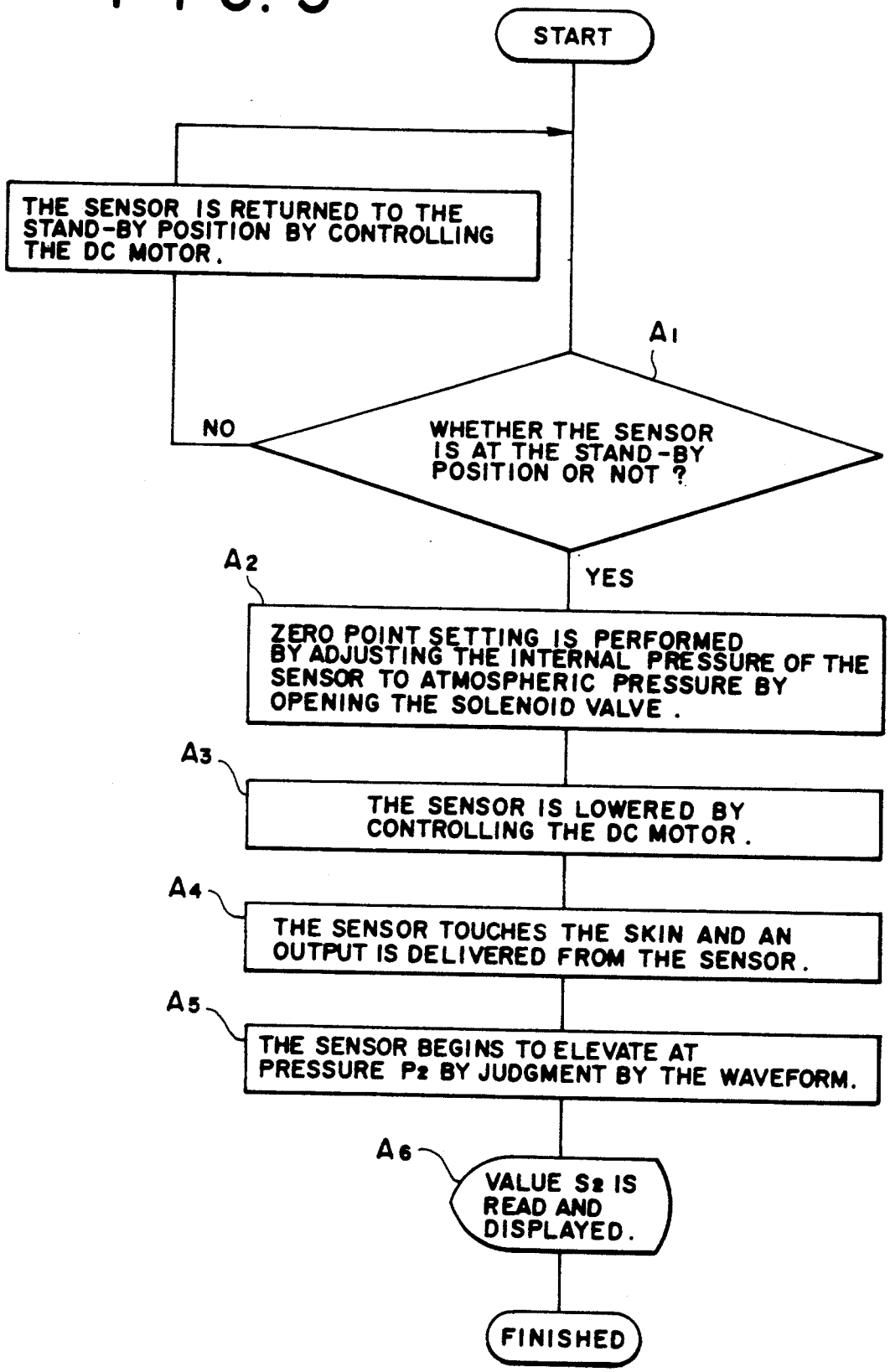
FIG. 3 is a flow chart showing the measurement procedure.

A method for measuring intracranial pressure by using the thus constituted device for measuring intracranial pressure will be described in the following. As shown in the flow chart in FIG. 3, the first step (Step $A_1$) is to check whether or not the pressure sensor is at the upper limit position or the stand-by position (the state shown in FIG. 1).

Next, the pressure detector B is mounted on the skin 16, under which the reservoir 40 is implanted, through the leg 1b, the center of the flexible membrane 5 is made to coincide with the center of the spherical dome 40a and the frame 1 is held perpendicular to the skin by lightly supporting the frame 1 by hand.

At this point, proper adjustment is made by loosening the thumbscrew 1b so that there is a proper distance between the flexible membrane 5 and the skin 16.

Then the internal pressure of the flexible membrane is adjusted to be the same as atmospheric pressure by opening the solenoid valve 7 by the switch control of the controller 35 (Step $A_2$). The solenoid valve 7 is closed in about 10 seconds.

Next, the pressing part 3 is lowered at a constant speed by driving the DC motor 2 by the switch control of the controller 35 (Step $A_3$).

As the pressing part 3 lowers, the flexible membrane 5 presses against the spherical dome 40a through the skin 16 and an output is delivered from the pressure sensor (Step $A_4$).

At the point when it is detected by judgment by the waveform that the pressure has reached the maximum level $P_2$, the pressing part 3 is elevated (inversion) at a constant speed by the inverse control of the DC motor 2 by means of the controller 35 (Step $A_5$). Pressure $S_2$ as intracranial pressure is read during the elevation of the pressing part 3 (Step $A_6$).

Detailed description is omitted of the changes in the pressure from the point when the flexible membrane 5 begins to be pressed against the spherical dome 40a by the lowering of the pressing part 3 to the point when the flexible membrane moves apart or separates from the spherical dome 40a because they are the same as the conventional ones described hereinabove with reference to FIGS. 7 and 8.

Figure 5:
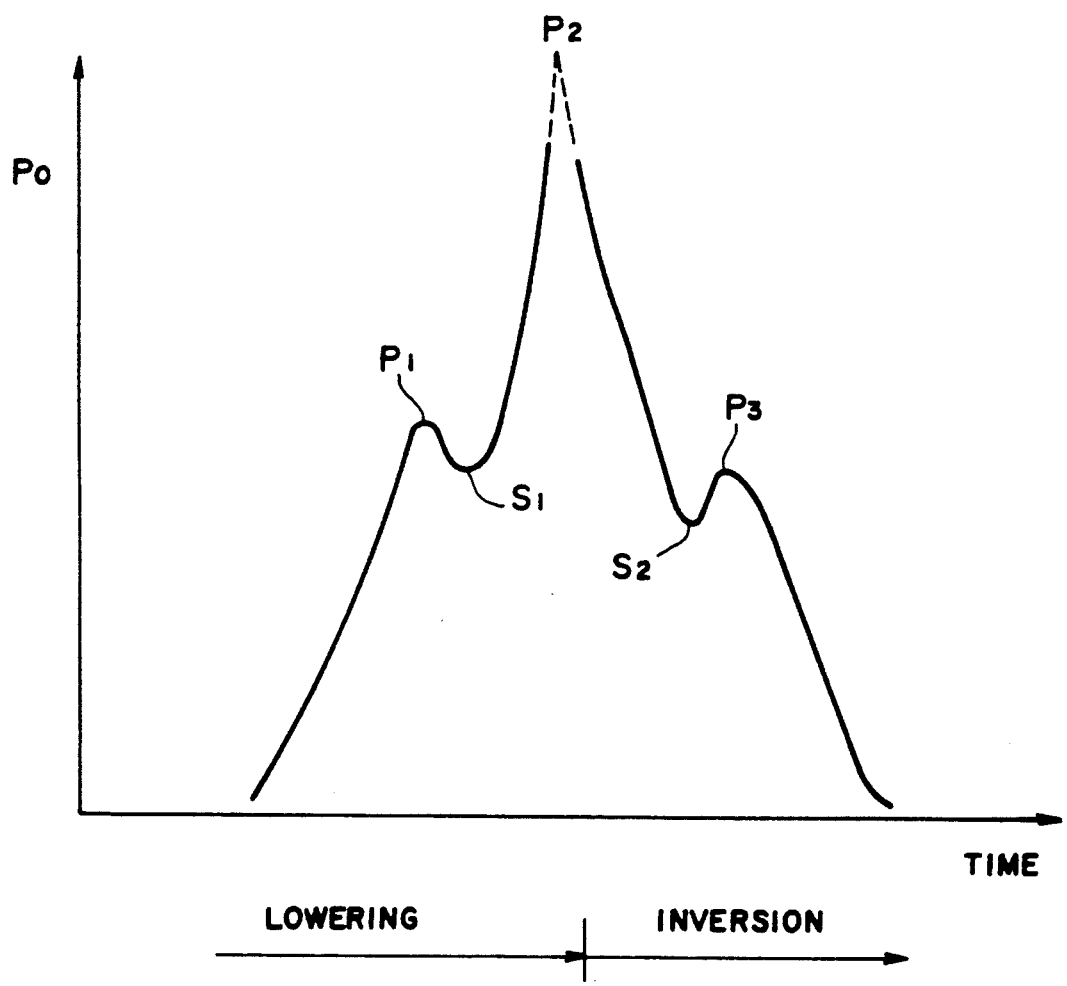
Figure 6:
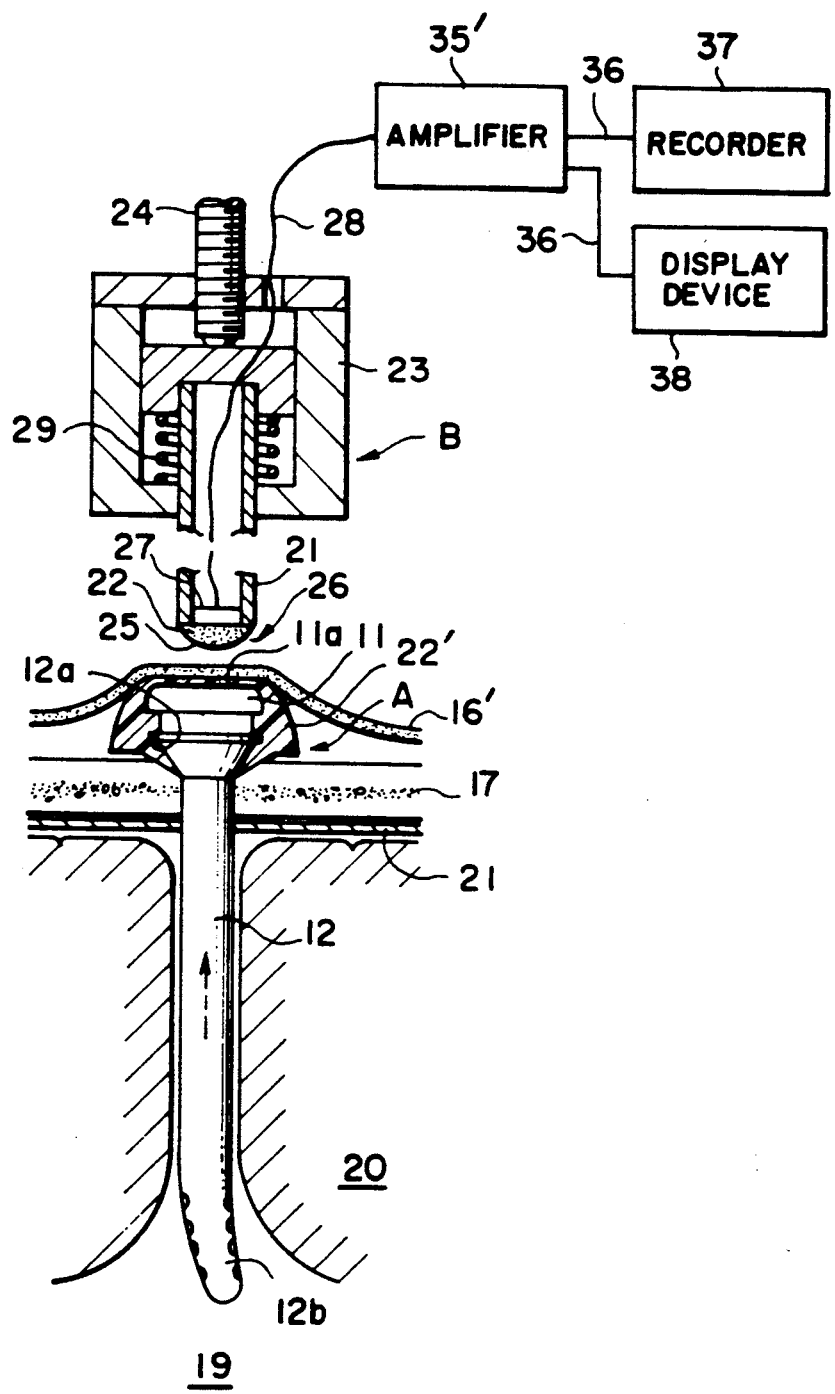
FIGS. 6 to 8 indicate a conventional method for measuring intracranial pressure and a device for the same.
Figure 7A:
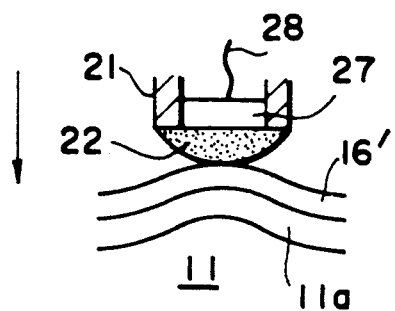
Figure 7B:
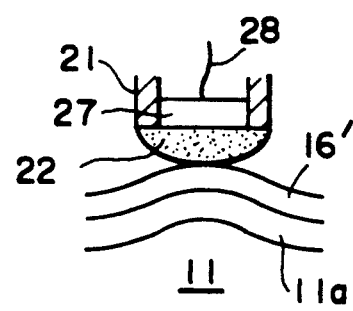
Figure 7C:
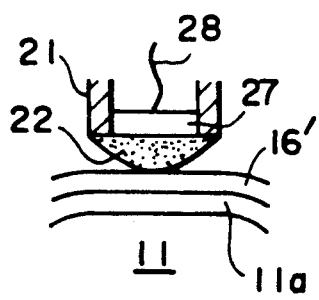
Figure 7D:
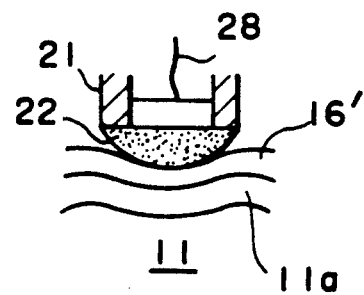
Figure 8:
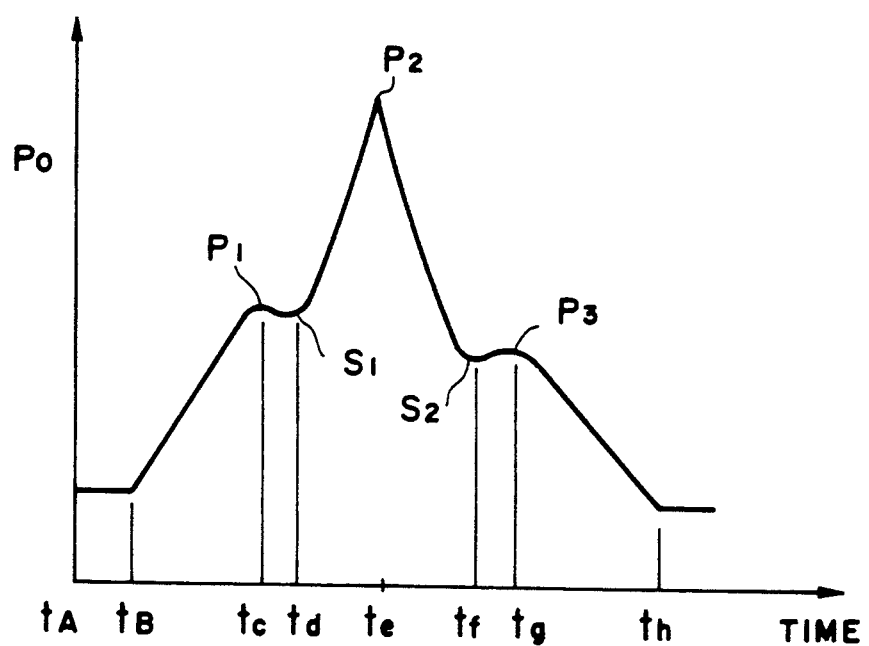

FIG. 5 shows an example of the thus obtained measurement record and each symbol in FIG. 5 corresponds to the same symbol in FIG. 8. In this case, the pressure $S_2$ read by the controller 35 is the intracranial pressure since zero point correction has been performed immediately before measurement.

Since the flexible membrane 5 is filled with air and its pressure is detected by the pressure transducer 6 as mentioned above, high-sensitivity pressure detection is possible and improved measurement precision is achieved in cases of thick skin.

Since zero point correction of the pressure transducer 6 is performed immediately before measurement while communicating the interior of the flexible membrane 5 with the atmosphere, pressure fluctuations due to temperature changes or the like are corrected thereby enabling improved measurement precision.

Since the interior of the flexible membrane 5 can be made to open into the atmosphere, pressure differences resulting from differences in the amount of the fluid filled in the flexible membrane 5 and pressure differences resulting from the expansion or contraction of the flexible membrane 5 due to temperature changes can be corrected thereby resulting in improved pressure measurement precision and reproducibility.

It is also advantageous that the above mentioned zero point correction of the pressure transducer 6 is easily performed by opening and closing a valve communicating with the interior of the flexible membrane 5.

Since the above valve consists of the solenoid valve 7 and it is accurately opened and closed by means of the controller 35, zero point correction of the pressure transducer 6 is easily performed.

Furthermore, the driving means equipped with the motor which presses the pressing part 3 having at its tip the flexible membrane 5 at a constant speed enables smoother operation of the pressure sensor consisting of the pressure transducer 6 and the flexible membrane 5 as compared to a manual operative method and also enables stable pressure measurement.

Since the driving means is constituted of the nut 3a attached to the movable pressing part 3 and the motor 2 having the revolving shaft 2a provided with a male thread fitting the nut 3a, the pressing part can easily be moved vertically at a constant speed.

In addition, since the leg 1a to be mounted on the skin of a human body is attached to the tip portion of the cylindrical frame 1 as a pressure detector main body, this device can stably be mounted on the human body.

Although air is used as the fluid which is filled in the flexible membrane 5 in the above example, it is self-evident that the same effect can be obtained using a liquid such as silicone oil. In that case, the exhaust port of the solenoid valve should be provided with a reservoir tank capable of accommodating silicone oil.

Although intracranial pressure is measured in the reservoir implanted in the chest or the like of a patient in the above example, it is a matter of course that intracranial pressure can be measured, as in the foregoing conventional example, in the brain ventricle port 41 used as a reservoir by the same procedure.

As mentioned above in detail, a method for measuring intracranial pressure and a device for the same according to this invention have the following effects or advantages.

(1) No calibration of measurement data is required and accurate measurements of intracranial pressure are obtained since zero point correction of a pressure transducer is performed by previously communicating the interior of a flexible membrane, which is provided at the tip of a pressing part to be pressed against a flexible spherical dome through the skin of a human body, with the atmosphere.

(2) The zero point correction of the pressure transducer is easily performed by opening and closing a valve communicating ambient atmosphere with the interior of the flexible membrane.

(3) A driving means which presses the pressing part at a constant speed enables smoother operation of a pressure sensor consisting of the pressure transducer and the flexible membrane as compared to a manual operative method and also enables stable pressure measurement.

(4) Since the interior of the above flexible membrane can be made to open into the atmosphere, pressure differences resulting from differences in the amount of a fluid filled in the flexible membrane and pressure differences resulting from the expansion or contraction of the flexible membrane due to temperature changes can be corrected thereby resulting in improved pressure measurement precision and reproducibility.

(5) The zero point correction of the pressure transducer is easily performed since the above valve consists of a solenoid valve and it is accurately opened and closed by means of a controller.

(6) The pressing part can easily be moved vertically at a constant speed since the driving means is constituted of a nut attached to a movable probe and a motor having a revolving shaft provided with a male thread fitting the nut.

(7) This device can stably be mounted on a human body since a leg to be mounted on the skin of the human body is attached to the tip portion of a cylindrical frame as a pressure detector main body.

We claim:

1. A method for measuring intracranial pressure by using a device comprising a reservoir implantable under the skin of a patient and into which cerebrospinal fluid can be introduced from a brain ventricle of the patient, a flexible dome configured to be upwardly projected from said reservoir by the pressure of the cerebrospinal fluid and flexibly deformable according to an external force, a pressing part for pressing against said dome through the skin, a pressing-part-driving means for driving said pressing part toward said dome at a constant speed, a pressure transducer for measuring the force of the pressing part pressing the dome and a flexible membrane provided at the tip of the pressing part and having an interior filled with a fluid, the method comprising: pressing the flexible membrane of the pressing part against the dome of the reservoir through the skin by means of the pressing-part-driving means after a zero point correction of the pressure transducer is performed by communicating the interior of the flexible membrane with the atmosphere.

2. A method for measuring intracranial pressure as set forth in claim 1, wherein the zero point correction of the pressure transducer is performed by opening a valve communicating the interior of the flexible membrane with the atmosphere and then closing the valve.

3. A device for measuring intracranial pressure of cerebrospinal fluid in a brain ventricle of a patient, comprising: a reservoir implantable under the skin of a patient and into which cerebrospinal fluid can be introduced from a brain ventricle of the patient, a flexible dome configured to be upwardly projected from said reservoir by the pressure of the cerebrospinal fluid and flexibly deformable according to an external force, and a detector comprising a pressing part movable to be pressed against said dome through the skin, a pressing-part-driving means for driving the pressing part toward the dome at a constant speed, a pressure transducer for measuring the force of the pressing part pressing the dome, a flexible membrane provided at the tip of the pressing part and having an interior filled with a fluid, means defining an exhaust path for communicating the interior of said flexible membrane with the atmosphere, and a valve for opening and closing said exhaust path.

4. A device for measuring intracranial pressure as set forth in claim 3, wherein the detector has a cylindrical frame, the pressing part being vertically movably fitted inside said frame, and the pressing-part-driving means comprising a nut attached to a rear end of the pressing part and a motor having a revolving shaft provided with a male thread fitting said nut.

5. A device for measuring intracranial pressure as set forth in claim 4, wherein a leg to be mounted on the skin of a patient is attached to the cylindrical frame.

6. A device for measuring intracranical pressure as set forth in claim 5, including means including a thumbscrew for adjusting the position of the leg relative to the cylindrical frame.

7. A device for measuring intracranial pressure as set forth in claim 3 or 4, wherein the means defining an exhaust path comprises an exhaust pipe communicating with the interior of the flexible membrane, the valve being provided in said exhaust pipe.

8. A device for measuring intracranial pressure as set forth in claim 3, wherein the valve comprises a solenoid valve, and a controller for controlling the solenoid valve.

9. A device for measuring the pressure of cerebrospinal fluid in a brain ventricle of a patient, comprising: a reservoir implantable under the skin of a patient during use of the device and having a flexible dome portion for receiving therein cerebrospinal fluid under pressure from a brain ventricle of the patient; and a detector positionable in opposed spaced relation from the implanted reservoir during use of the device for detecting the pressure of the cerebrospinal fluid, the detector comprising a flexible membrane having an interior, means including a conduit connected to the flexible membrane for selectively communicating the interior of the flexible membrane with ambient air to equalize the air pressure within the flexible membrane with that of the ambient air and for thereafter fluidtightly closing the conduit to maintain the flexible membrane filled with air, means mounting the flexible membrane for displacement toward and away from the flexible dome portion of the reservoir, driving means for displacing the air-filled flexible membrane toward the reservoir to cause the flexible membrane to exert an inward pressing force on the flexible dome portion of the reservoir through the patient's skin to flexibly inwardly deform the dome portion, and means for measuring the force with which the flexible membrane presses against the flexible dome portion and producing a corresponding output signal representative of the pressure of the cerebrospinal fluid.

10. A device according to claim 9; wherein the means for measuring the force comprises a pressure transducer connected to measure the air pressure within the flexible membrane and produce a corresponding electrical output signal.

11. A device according to claim 9; wherein the means mounting the flexible membrane comprises a displaceable member having forward and rearward ends, the flexible membrane being mounted at the forward end of the displaceable member, and means mounting the displaceable member for displacement toward and away from the flexible dome portion of the reservoir to thereby correspondingly displace the flexible membrane.

12. A device according to claim 11; wherein the means mounting the displaceable member comprises a frame positionable on the patient in opposed spaced relation from the implanted reservoir during use of the device, the displaceable member being slidably mounted on the frame to undergo displacement toward and away from the flexible dome portion.

13. A device according to claim 12; including means for mounting the driving means on the frame.

14. A device according to claim 13; wherein the driving means comprises means including a motor for displacing the displaceable member at a constant speed toward the flexible dome portion of the reservoir.

15. A device according to claim 9; wherein the driving means comprises means including a motor for displacing the flexible membrane at a constant speed toward the flexible dome portion of the reservoir.

16. A device according to claim 15; wherein the means for selectively communicating the interior of the flexible membrane with the ambient air comprises a valve disposed in the conduit for opening and closing the conduit.

17. A device according to claim 16; including control means for controlling the operation of the motor and the valve.

18. A device according to claim 17; wherein the motor comprises an electrically operated motor and the valve comprises an electrically operated valve, and the control means comprises a controller for electrically controlling the operation of the motor and the valve.

19. A device according to claim 16; wherein the means for measuring the force comprises a pressure transducer connected to measure the air pressure within the flexible membrane and produce a corresponding electrical output signal.

20. A device according to claim 19; including means responsive to the electrical output signal from the pressure transducer for providing a recording of the pressure of the cerebrospinal fluid.

* * * * *